United States Patent [19]

Erker

[11] Patent Number: 4,620,313
[45] Date of Patent: Oct. 28, 1986

[54] CONTROLLED CUTOFF FREQUENCY ANALOG FILTER FOR CT SCANNERS

[75] Inventor: Joseph W. Erker, Aurora, Ohio

[73] Assignee: Technicare Corporation, Solon, Ohio

[21] Appl. No.: 622,522

[22] Filed: Jun. 20, 1984

[51] Int. Cl.$^4$ .................................... G03B 41/16
[52] U.S. Cl. .................................. 378/19; 378/4; 378/901
[58] Field of Search ............... 378/4, 19, 901; 364/414

[56] References Cited

U.S. PATENT DOCUMENTS

| | | |
|---|---|---|
| 4,034,223 | 7/1977 | Kowalski .......................... 378/901 |
| 4,181,858 | 1/1980 | Moore .............................. 378/15 |
| 4,494,141 | 1/1985 | Altebruse ......................... 378/19 |

OTHER PUBLICATIONS

C. B. Lim et al., "CT Image Noise and Resolution Behavior in RC Filter—Based Projection Data Acquisition", *IEEE Transactions on Nuclear Science*, vol. NS-28, No. 1, Feb. 1981.

R. N. Bracewell, *The Fourier Transform and its Applications*, New York, McGraw—Hill, pp. 189-197.
"MF10 Universal Monolithic Dual Switched Capacitor Filter", *National Semiconductor Corp.*, Dec. 1981, Product Brochure, IM-B25M121.

*Primary Examiner*—Craig E. Church
*Attorney, Agent, or Firm*—Audley A. Ciamporcero, Jr.; Michael A. Kaufman

[57] ABSTRACT

A network for use in a fourth generation CT scanner for noise reduction. The network comprises an active low pass filter whose cutoff frequency is controlled by a scaled signal responsive to the angular velocity of the rotating radiation source of the scanner. In a preferred embodiment a raw signal is generated by an encoder that detects movement of the source. As the source speed changes either in response to an operator's selection of a different scan speed or to systemic variations in the scanner relative to expected performance, the filter's cutoff frequency will automatically change thereby assuring optimum performance regardless of scan speed.

5 Claims, 2 Drawing Figures

CONTROLLED CUTOFF FREQUENCY ANALOG FILTER FOR CT SCANNERS

TECHNICAL FIELD

This invention relates generally to computed tomographic or CT scanners of the type having a rotational X-ray source and, in particular, to conditioning signals detected by such scanners prior to processing those signals into tomographic images.

BACKGROUND OF THE INVENTION

Since about 1978 rotational type CT scanners which can perform a scan of a single planar slice of a patient in as little as two seconds have been commercially available. The quest for speed in the data acquisition phase of medical CT scanners has been of substantial concern to designers and users of CT scanners for the obvious reasons of economy and image quality. Due to variations in the motions of various organs and anatomical functions in human beings, the influence of speed on image quality varies depending on the particular section of the patient being scanned. Thus, to provide added flexibility to the user, such modern CT scanners typically offer a choice of scan speeds, for example, 2, 4, and 8 seconds.

One popular configuration of these modern CT scanners is the so-called fourth generation system which includes a rotational source of radiation adapted to emit a fan beam of radiation typically directed at a patient supported within a scan circle, a stationary arc of uniformly spaced detectors about the center point of the scan circle, a data acquisition system and an image processor. In such scanners, the radiation source is rotated about the object to be imaged while emitting a beam of radiation of measured intensity. The array of detectors produce analog electrical signals proportional to the intensity of radiation incident on them. These signals are processed and sampled, typically once for every 96th of a degree of rotation of the source and subsequently reconstructed digitally into a planar image of the scanned slice.

It turns out that the temporal frequency content of a detector signal is determined not only by the spatial frequency content of the object under examination, but also by the angular velocity of the radiation source. Thus, under the controlled condition of constant dose, the same object will result in varying noise behavior for different scan speeds. See, for example, "CT Image Noise and Resolution Behavior in RC Filter-Based Projection Data Acquisition" by C. B. Lim, et al., in *IEEE Transactions on Nuclear Science*, Vol. NS-28, No. 1, February 1981, p. 152 et seq.

Regardless of the surce of the frequency content of the analog signal generated by the array of detectors, the high frequency content, essentially noise in the system, must be eliminated. Otherwise, when the signal is sampled, some of these high frequency components will appear impersonating low frequencies, a well known phenomena known as "aliasing". According to the sampling theorem, in a function having a finite limit in its rate of change, essentially all information may be recovered by fine sampling of a band limited portion of the function, Bracewell, R. N., 1965 *The Fourier Transform and its Applications*, New York, McGraw Hill, page 189 et seq. In prior CT scanning systems, the band limiting function was typically accomplished by filtering the analog detector signals by a fixed cut-off frequency analog filter where the cut-off frequency selection was dependent on the geometry of the specific CT system and the angular velocity of the scanner. Such designs are inherently limited in systems with either appreciable variations in the actual angular velocity relative to expected angular velocity of the source or in systems offering a choice of scan speeds. Since the cut-off filter has to be designed to accommodate the worst case situation, whatever the chosen cut-off frequency is, it can only approach optimum result for a single scan speed.

SUMMARY OF THE INVENTION

I have invented a noise reduction network for use in rotational type CT scanners utilizing a variable cut-off frequency filter for band limiting the analog detector signal data in which the cut-off frequency is controlled by and made dependent on the actual rotational velocity of the rotating X-ray source. In a preferred embodiment, a position detecting incremental encoder is used to monitor the angular velocity of the rotational source and the signal produced by this encoder is processed and applied as a control signal to a switched capacitor low pass filter in which the cutoff frequency of the filter is determined by the control signal.

DETAILED DESCRIPTION OF THE PREFERRED EMBODIMENTS INCLUDING THE BEST MODE

Figure 1:
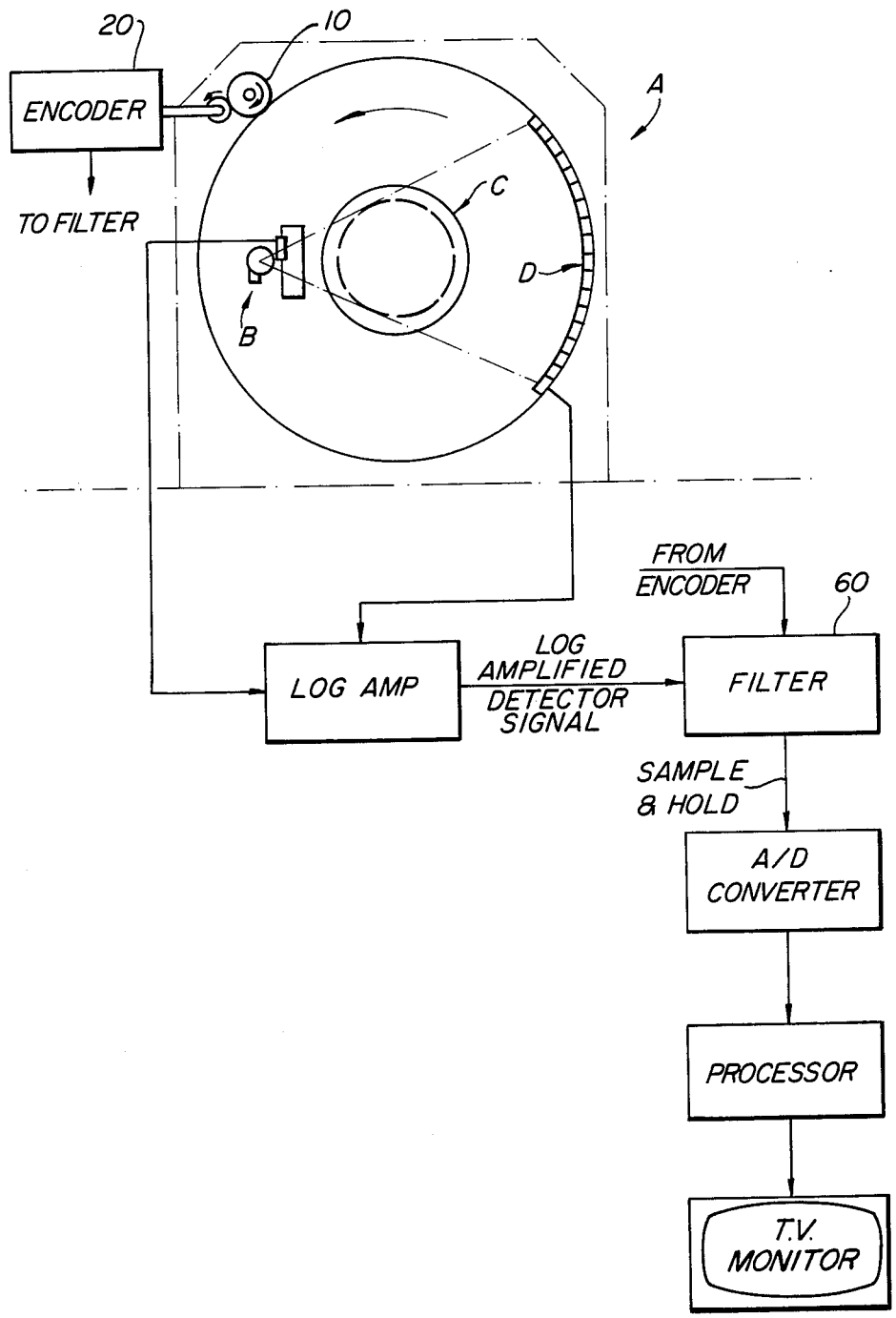
FIG. 1 is a schematic system block diagram showing a rotating fan beam tomographic scanner.

FIG. 1 illustrates a rotating fan beam tomographic scanner A, which includes a source of radiation B for subjecting a planar region of a patient to penetrating radiation. The patient is disposed, typically in a supine position, within opening C. The scanner further comprises an array of radiation detectors D, which typically forms a circular ring about patient position opening C at a sufficient radius to permit radiation source B to rotate therewithin. The signal output by the detectors is conditioned and applied to a processor which implements algorithms well known in the tomographic art to produce a visual image representation of the planar region of the patient being examined.

Figure 2:
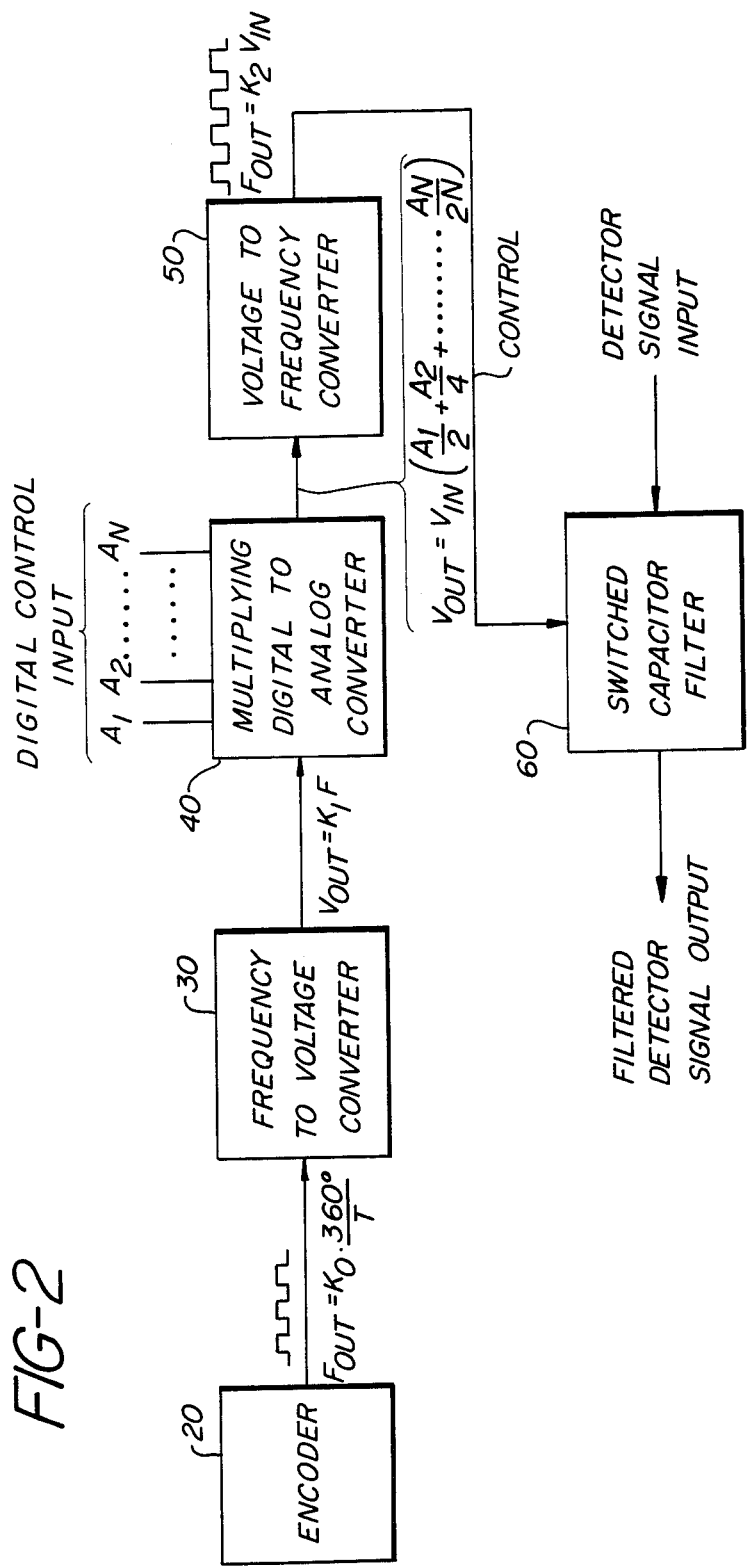
FIG. 2 is a preferred embodiment of the present invention in block diagram form for use in a CT scanner of the type shown in FIG. 1.

Relative motion between the source of radiation B and the detectors is caused by mechanical means 10 for moving the radiation source. In a scanner of the type shown in FIG. 1, the speed of this movement is under operator control by remote electrical signal control permitting the operator to select scan speeds typically 2, 4 and 8 seconds. Connected to this means for moving the rotational source is a position indicating device such as incremental encoder 20 which, in conventional fashion, is programmed to output a rectangular pulse train, as shown in FIG. 2, whose frequency is functionally dependent on the angular velocity of the source. The particular encoder 20 shown in FIG. 2 generates a rectangular pulse for each angular increment that the rotating source traverses in a fixed period of time. In other words, the output frequency $F_{out}$ of the encoder is a constant, $K_O \times 360°$ per unit of time, T:

$$F_{out} = K_0 \frac{360°}{T} \quad (1)$$

The pulse train generated by encoder 20 is then applied to a frequency-to-voltage converter 30 such as the model 453K available from Analog Devices. The frequency-to-voltage converter 30 converts the encoder generated pulse train into a voltage signal having a 10 volt peak amplitude that is proportional to the frequency of the incoming pulse train.

In the embodiment disclosed in connection with FIG. 2, the output voltage of the frequency-to-voltage converter 30 is related to the frequency of the encoder pulse train by a constant, $K_1$. Assuming a sampling interval of one 96th of a degree per scan, a 360° scan requires 34,560 samples (360×96). Thus, a two second scan requires 17,280 samples per second or a sampling frequency of 17.28 KHz. Similarly, a four second scan suggests a frequency of 0.864 KHz while an eight second scan suggests 0.432 KHz. Since the peak voltage is ten for the Analog Devices converter, $K_1$ in this system equals 0.579 volts per KHz (10÷17.28). The output voltage of the frequency-to-voltage converter 30 is thus proportional to the angular velocity of the rotating source.

The output voltage generated by the frequency-to-voltage converter 30 is applied to a digitally switched attenuator, or a multiplying digital-to-analog converter 40 such as Model DAC1020 available from National Semiconductor. The multiplying digital-to-analog converter 40 issues an attenuated output voltage that is directly related to the input voltage, digitally attenuated by bits $A_1$ to $A_N$ in accordance with the following relationship:

$$V_{out} = V_{in}(A_1/2 + A_2/4 + \ldots + A_N/2N) \quad (2)$$

The selection of bits $A_1$ to $A_N$ is under software control. The input voltage to the multiplying digital-to-analog converter is proportional to the Nyquist frequency or one-half the highest frequency permissible under the sampling theorem and consistent with the sampling rate limits of the system. Therefore, the Nyquist frequency is ½ of 17.28 KHz or 8.64 KHz. The multiplying digital-to-analog converter 40 establishes the fraction of Nyquist that will be selected as the −3 dB point, that is, the point defining the cutoff frequency of a filter. In a preferred embodiment this fraction is chosen as one half. This is accomplished by setting the most significant bit $A_1$ to 1 and setting all of the other bits $A_2$ to $A_n$ to 0.

The output voltage of the multiplying digital-to-analog converter is then reconverted to frequency form by a voltage-to-frequency converter 50 such as Model 4707 available from Teledyne Philbrick. The output of the voltage-to-frequency converter 50 is a pulse train whose frequency is proportional to the input voltage, $V_{in}$, by a constant factor of $K_2$.

The pulse train generated by the voltage-to-frequency converter serves as the control signal 61 to a switched capacitor filter 60 such as the Model MF10 Universal Monolithic Dual Switched Capacitor Filter, available from the National Semiconductor Corporation. The frequency of this pulse train is a clock pulse which determines the cutoff frequency, $f_c$, of the low pass output of the switched capacitor filter 60. In this case, $f_c$ is related to the frequency of the pulse train control signal by the fraction 1/100, the constant $K_2$ is conveniently selected to be 100.

Since the filter cutoff frequency control signal, as well as the signal sampling frequency are a function of the angular velocity of the radiation source, the filter is optimally designed to accommodate variations in the angular velocity of the source. The filter automatically changes its cutoff frequency as a function of angular velocity in such a way as to maintain the ratio of filter cutoff frequency to Nyquist frequency constant. Thus when the detector signal is applied to the switched capacitor filter, the filter automatically attenuates the undesirable high frequency components to a level that produces insignificant aliasing. In other words, the level of aliased information in the sampled signal is no longer dependent on variations in the angular velocity of the rotating source.

The data that is subject to the variable cutoff frequency filter is obtained from a network denoted as LOG AMP 70. This network, in conventional fashion, converts the electrical signals detected by detectors D into amplified logarithmic signals which are compared to the intensity of the beam emitted by the source to thereby permit calculation of attenuation through the patient. After the signal is filtered by active filter 60, it is subject to data sampling and, in conventional fashion, conversion to digital form by an analog-to-digital converter such as A/D converter 80. The digital values are then processed in known fashion by an image processor such as processor 90 for subsequent image display, for example, on T.V. monitor 100.

While the above-described subsystem was discussed in connection with a specific type of variable control cutoff filter wherein cutoff frequency is functionally related to the angular velocity of the rotational source, it will be appreciated that other types of active filters may be used toward the same end. Similarly, the control signal establishing the cutoff characteristics of the selected filter need not be the velocity of the source but may be some other time dependent signal.

I claim:

1. An X-ray computed tomographic scanner for reconstructing an image of a region of an object positioned in a scan circle from filtered data sampled at a preselected frequency comprising:
 (a) a source of X-radiaiton rotating at an angular velocity about said scan circle for radiating the scan circle with a beam of radiation of preselected intensity from a plurality of directions;
 (b) an array of radiation detectors disposed about the scan circle positioned to receive transmitted radiation emitted by said source and having traversed the scan circle and to convert said received radiation into signals proportional to their intensity, said signals having a temporal frequency content functionally related to the angular velocity of the source;
 (c) position indicating means operatively connected to said rotating source for detecting the angular velocity of said source;
 (d) data acquisition means for collecting the converted signals from said radiation detectors, said signals generally having a high frequency component and wide band quantum noise which contribute to degradation of reconstructed images;
 (e) active analog filter means responsive to said position indicating means having a variable cutoff frequency automatically set as a predetermined fraction of the detected angular velocity of said source such that the frequency content of the filtered collected data essentially contains no frequencies above ½ the data sampling frequency;

(f) sampling means for sampling the filtered data at a preselected frequency; and (g) means for reconstructing an image of the scanned region of the object from the sampled data.

2. The computed tomographic scanner according to claim 1 wherein said position indicating means is an encoder whose output is a pulse train of a frequency related to the angular velocity of the rotating source.

3. The computed tomographic scanner according to claim 2 further comprising means operatively connected to said encoder for scaling the frequency of the pulse train and for applying said scaled pulse train to said active filter means.

4. The computed tomographic scanner according to claim 3 wherein said scaling means includes:

(a) a frequency to voltage converter connected to said encoder for receiving the pulse train output of said encoder and for converting said pulse train into an analog voltage signal functionally related to a predetermined fraction of the frequency of the encoder pulse train;

(b) a digitally switched attenuator connected to receive the analog voltage signal generated by said frequency to voltage converter and for producing an analog voltage signal whose amplitude is proportional to the output of the frequency to voltage converter scaled by a preselected digital factor; and (c) a voltage to frequency converter operatively connected to said attenuator for converting the output of the digitally switched attenuator to a pulse train of a frequency functionally related to the voltage output by said attenuator.

5. The tomographic scanner according to claim 1 wherein said active filter means is a switched capacitor filter.

* * * * *